US006248524B1

(12) United States Patent
Krontiris et al.

(10) Patent No.: US 6,248,524 B1
(45) Date of Patent: Jun. 19, 2001

(54) DISEASE ASSOCIATION BY LOCUS STRATIFICATION

(75) Inventors: Theodore G. Krontiris, Pasadena; Garry P. Larson, San Dimas; Steven D. Flanagan, Running Springs, all of CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 09/161,540

(22) Filed: Sep. 28, 1998

Related U.S. Application Data (60) Provisional application No. 60/060,285, filed on Sep. 29, 1997.

(51) Int. Cl.⁷ .............................. C12Q 1/68; C12P 19/34; C07H 21/02; C07H 21/04

(52) U.S. Cl. ........................... 435/6; 435/91.1; 435/91.2; 536/23.1

(58) Field of Search .............................. 435/7.23, 6, 91.2, 435/91.1; 514/44; 536/23.1

(56) References Cited

U.S. PATENT DOCUMENTS 5,912,127 * 6/1999 Narod et al. .............................. 435/6

FOREIGN PATENT DOCUMENTS

| WO 96 36691 | 11/1996 | (WO) . |
| WO 97 47772 | 12/1997 | (WO) . |
| WO 98 25125 | 6/1998 | (WO) . |

OTHER PUBLICATIONS

Phelan, C.M. et al., Ovarian cancer risk in BRCA1 carriers is modified by the HRAS1 variable number of tandem repeat (VNTR) locus, Nature Genetics vol. 12, 309–311, Mar. 1996.*

Thomson, G. Mapping Disease Genes: Family–based association studies, American Journal of Human Genetics, vol. 57, 487–498, Mar. 1996.*

Phelan, C.M. et al., Ovarian cancer risk in BRCA1 carriers is modified by the HRAS1 variable number of tandem repeat (VNTR) locus, Nature Genetics vol. 12, 309–311, Mar. 15, 1996.*

Vorechovsky, I. et al., ATM Mutations in Cancer Families, Cancer Research, vol. 56, 4130–4133 Sep. 15, 1996.*

Mousses, S. et al. Two variants of the CIP/WAF1 gene occur together and are associated with human cancer, Human Molecular Genetics, vol. 4, 1089–1092, Mar. 28, 1995.*

Thomson, G. Mapping Disease Genes: Family–based association studies, American Journal of Human Genetics, vol. 57, 487–498, Apr. 18, 1995.*

Swift, M., Reitnauer, P. J., Morrell, D. and Chase, C. L., "Breast and Other Cancers in Families With Ataxia–Telangiectasia," New Eng. J. Med. 316:1289–1294 (1987).

Savitsky, K. et al., "A Single Ataxia Telangiectasia Gene With a Product Similar to PI–3 Kinase," Science 268:1749–1753 (1995).

Atham, P., Rappaport, R. and Swift, M., "Molecular Genotyping Shows That Ataxia–Telangiectasia Heterozygotes Are Predisposed to Breast Cancer," Cancer Genet. Cytogenet. 92:130–134 (1996).

Fitzgerald, M. G. et al., "Heterozygous ATM Mutations Do Not Contribute to Early Onset of Breast Cancer," Nature Genet. 15:307–310 (1997).

Vorechovsky, I. et al., "The ATM Gene and Susceptibility to Breast Cancer: Analysis of 38 Breast Tumors Reveals no Evidence for Mutation," Cancer Res. 56:2726–2732 (1996).

Vorechovsky, I. et al., "ATM Mutations in Cancer Families," Cancer Res. 56:4130–4133 (1996).

Kronitiris, T. G., Devlin B., Karp, D. D., Robert, N. J. and Risch, N., "An Association Between the Risk of Cancer and Mutations in the HRAS1 Minisatellite Locus," New Eng. J. Med. 329:517–523 (1993).

Phelan, C. M. et a.., "Ovarian Cancer Risk in BRCA1 Carriers is Modified by the HRAS1 Variable Number of Tandem Repeat (VNTR) Locus," Nature Genet. 12:309–311 (1996).

Harper, J. W., Adami, G. R., Wei, N., Keyomarsi, K. and Elledge, S. J., The p21 Cdk–Interacting Protein Cip1 is a Potent Inhibitor of G1 Cyclin–Dependent Kinases, Cell 75:805–816 (1993).

El–Deiry, W. S. et al., "WAF1, a Potential Mediator of p53 Tumor Suppression," Cell 75:817–825 (1993).

Chedid, M., Michieli, P., Lengel, C., Huppi, K. and Givol, D., A Single Nucleotide Substitution at Codon 31 (ser/ag) Defines a Polymorphism in a Highly Conserved Region of the p53–Inducible WAF1/CIP1, Oncogene 9:3021–3024 (1994).

Mousses, S., Ozcelik, H., Lee, P. D., Malkin, D., Bull, S. B. and Andrulis, I. L., "Two Variants of the CIP1/WAF1 Gene Occur Together and Are Associated With Human Cancer," Hum. Molec. Genet. 4:1089–1092 (1995).

Sjalander, A., Birgander, R., Rannug, A., Alexandrie, A.–K., Tornling, G. and Beckman, G., "Association Between the p21 Codon 31A1 (arg) Allele and Lung Cancer," Hum. Hered. 46:221–225 (1996).

Morgan, S. E., et al., "Fragments of ATM Which Have Dominant–Negative or Complementing Activity," Mol. Cell. Biol. 17:2020–2029 (1997).

Scully, R. et al., "Association of BRCA1 With Rad51 in Mitotic and Meiotic Cells," Cell 88:265–275 (1997).

(List continued on next page.)

Primary Examiner—Stephanie Zitomer
Assistant Examiner—Cynthia B. Wilder
(74) Attorney, Agent, or Firm—Rothwell, Figg, Ernst & Manbeck (57) ABSTRACT

Pathogenetic allele variants that predispose to a disease can be identified by stratifying affected sib pairs by allele-sharing statuss at two or more candidate loci. This locus stratification method has been used to identify an allelic variant at the ATM locus which is implicated in breast cancer.

9 Claims, 2 Drawing Sheets

OTHER PUBLICATIONS

Sharan, S. K. et al., "Embryonic Lethality and Radiation Hypersensitivity Mediated by Rad51 in Mice Lacking Brca2," *Nature* 386:804–810 (1997).

Shafman, T. et al., "Interaction Between ATM Protein and c–Ab1 in Response to DNA Damage," *Nature* 387:520–523 (1997).

Buffone, G. J., "Isolation of DNA From Biological Specimens Without Extraction with Phenol," *Clin. Chem.* 31:164–165 (1985).

Hacia, J. G., et al., "Detection of Heterozygous Mutations in Brca1 Using High Density Oligonucleotide Arrays and Two–Color Fluorescence Analysis," *Nat. Genet.* 14(4):441–447 (1996).

Larson, G. P. et al., "An allelic variant at the ATM locus is implicated in breast cancer susceptibility", *American J. of Human Genetics,* vol. 61, No. 4 Suppl., Oct. 1997, p. A71.

Krontiris, T. G., "Minisatellites as modifier genes", *Proceedings of the American Assoc. for Cancer Research Annual Meeting,* vol. 38, No. 0, Apr. 12–16, 1997, p. 650.

Kerangueven, F. et al., "Loss of heterozygosity in human breast carcinomas in the ataxia telangiectasia, Cowden disease and BRAC1 gene regions", *Oncogene,* vol. 14, No. 3, Jan. 1997, pp. 339–47.

Wapelhorst, B. et al., "Linkage and association studies in insulin dependent diabetis with a new dinucleotide repeat polymorphism at the GAD65 locus", *Autoimmunity,* vol. 21, 1995, pp. 127–130.

Curtis, D., "Use of siblings as controls in case–control association studies", *Annals of Human Genetics,* vol. 61, No. 4, Jul. 1997, pp. 319–333.

Larson, G. et al., "An allelic variant at the ATM locus is implicated in breast cancer susceptibility", *Genetic Testing,* vol. 1, No. 3, 1998, pp. 165–170.

Wright, J. et al., "A high frequency of distinct ATM gene mutations in ataxia–telangiectasia", *American J. of Human Genetics,* vol. 59, Oct. 1996, pp. 839–846.

Vorechovsky, I. et al., "The ATM gene and susceptibility to breast cancer: analysis of 38 breast tumors reveals no evidence for mutation", *Cancer Research,* vol. 56, No. 12, Jun. 1996, pp. 2726–2732.

Krontiris, T. G. et al., "An association between the risk of cancer and mutations in the HRAS1 minisatellite locus", *The New England J. of Medicine,* vol. 329, No. 8, Aug. 19, 1993, pp. 517–523.

Thom son, G., "Mapping disease genes: Family based assoc. studies," *American J. of Human Genetics,* vol. 57, No. 2, 1995, pp. 487–498.

Benjamin, J., et al., "Population and familial association between the D4 dopamine receptor gene and measres of novelty seeking", *Nature Genetics,* vol. 12, No. 1, 1966, pp. 81–84.

Vorechovsky, I. et al., ATM Mutations in Cancer Families, Cancer Research, vol. 56, 4130–4133, Sep. 1996.*

Mousses, S. et al. Two variants of the CIP/WAF1 gene occur together and are associated with human cancer, Human Molecular Genetics, vol. 4, 1089–1092, Mar. 1995.*

* cited by examiner

DISEASE ASSOCIATION BY LOCUS STRATIFICATION

CROSS REFERENCE TO RELATED APPLICATION

Benefit is claimed of U.S. Provisional application 60/060,285, filed Sep. 29, 1997.

STATEMENT REGARDING FEDERALLY-SPONSORED RESEARCH

This invention was made in the course of research funded in part by the United States National Institutes of Health Grant No. 1-RO1-CA45052. The U.S. government may have certain rights in the invention.

BACKGROUND

This invention relates to the field of genetic markers for disease.

In most cases the complex genetic contribution to cancer and other disease susceptibility remains to be elucidated. Efforts have focused on identification of potentially pathogenetic allelic variants of individual candidate loci. To increase the probability of identifying such variants, this invention focuses on interaction of candidate loci. According to this invention, it is a candidate locus interaction, rather than simply a candidate gene inquiry, that serves as the principal means of discovery.

SUMMARY OF THE INVENTION

Our invention is a method for rapidly identifying pathogenetic allele variants present in the population-at-large that predispose to a disease or that are relevant to diagnosis, prognosis or treatment of a disease such as cancer. Our method initially relies on allele-sharing stratification of affected sib pairs to identify subgroups of cases bearing potentially pathogenetic alleles of that candidate locus. To increase the probability of identifying such variants, we further stratify the sib pairs by allele-sharing status at a second candidate locus that may demonstrate an epistatic interaction with the first candidate locus. If desired, the sib pairs may be further stratified by allele-sharing status at one or more additional candidate loci that may demonstrate an epistatic interaction with one or more of the other candidate loci. We refer to our method as disease association by locus stratification.

Using this method, a pathogenetic variant of the ATM locus which is associated with a 4.5 fold relative risk of breast cancer has been identified. This variant has a G for C substitution in exon 24 at the nucleotide which is numbered 3349 in Genbank accession no. U33841. (This is nucleotide number 3060 if numbering begins at the first nucleotide of the atg start codon, which is numbered 190 in Genbank accession no. U33841.) We refer to this pathogenetic variant as the ATM exon 24 variant.

BRIEF DESCRIPTION OF THE FIGURES

FIG. 1. Identification of heterozygotes for ATM Exon 24 variant in breast cancer sibs.

a, Representative Alw I RFLP analysis of exon 24 PCR fragments from homozygous (left, 6 lanes) and heterozygous (right) patients. Asterisk (*), heterozygote. MW, 100 bp ladder. b, Confirmation of heterozygote missense mutation (C→G) via sequence analysis of ATM exon 24 PCR product utilizing bidirectional fluorescent sequencing. Asterisk (*), location of G and C heterozygous site. ATM exon 24 includes the sequence TGATCCTTATTCAA (Seq. ID 1) in the coding strand as shown for homozygotes and the sequence TAAGGATCAGC (Seq. ID 2) in the non-coding strand as shown for homozygotes. ATM exon 24 variant includes the sequence TGATCGTTATTCAA (Seq. ID 3) in the coding strand as shown for heterozygotes and the sequence AACGATCAGCCTA (Seq. ID 4) in the non-coding strand as shown for heterozygotes.

FIG. 2. Identification of heterozygotes for CDKN1A variant in breast cancer sibs.

a, Representative Esm Al RFLP analysis of PCR fragments from homozygous (right, 3 lanes) and heterozygous (left) patients. Asterisk (*), heterozygote. MW, 100 bp ladder. b, Confirmation of heterozygote missense mutation (C→A) via sequence analysis of PCR product utilizing bidirectional fluorescent sequencing. Asterisk (*), location of C and A heterozygous site. CDKN1A contains the sequence CTGAGCCGCGACTGTGA (Seq. ID 5) in the coding strand as shown for homozygotes and the sequence TCGCGGCTCA (Seq. ID 6) in the non-coding strand as shown for homozygotes. CDKN1A variant contains the sequence CTGAGACGCGACTGTG (Seq. ID 7) in the coding strand as shown for heterozygotes and the sequence TCGCGTCTCA (Seq. ID 8) in the non-coding strand as shown for heterozygotes.

DETAILED DESCRIPTION OF THE PREFERRED EMBODIMENT

Ataxia telangiectasia (AT) is an autosomal recessive disorder in which a defect in DNA repair and radiation sensitivity are accompanied by cerebellar ataxia, immune deficits, telangiectasia, and predisposition to cancer. Heterozygotes have also been reported to be at increased risk of malignancy, particularly breast cancer[1]. Since the discovery of the gene at 11q23 responsible for the disorder, designated ATM[2], several subsequent investigations have yielded conflicting results in support of this association. Athma et al.[3], in a study of 99 AT families, showed that carriers identified by genetic markers tightly linked to ATM demonstrated an age-dependent relative risk of breast cancer between 2.9 and 6.4. In contrast, ATM mutation analysis in cases of sporadic breast cancer revealed no association[4,5]. Finally, some ATM mutations were observed in breast cancer cases with a positive, but unspecified, first-degree family history of cancer[6]. Since the foregoing studies suggested that the method of ascertainment of breast cancer cases was potentially critical to observing an effect, we analyzed 66 independent cases from sib pairs affected with breast cancer that had previously been collected during an investigation of pathogenetic-allele-sharing at the HRAS1 minisatellite locus. An exon 24 polymorphism of ATM,[5,6], substituting arginine for proline, was associated with breast cancer in these cases with an overall odds ratio of 4.5. In the presence of a rare HRAS1 allele, the odds ratio increased to 6.9. Several carriers of the ATM exon 24 polymorphism also possessed a cancer-associated, missense polymorphism of a gene considered downstream of ATM action, namely CDKN1A (p21$^{CIP1/WAF1}$). Thus, at least one allelic variant of ATM is associated in breast cancer when family history is taken into account, and the ATM locus may interact with both HRAS1 and CDKN1A.

We reasoned that sib pairs sharing 2 ATM chromosomes would be most likely to demonstrate pathogenetic alleles. Furthermore, if epistatic interactions of ATM with other cancer-associated loci acted to increase the risk of these pathogenetic variants, then further stratification of cases based on allele-sharing status at interacting loci might serve to identify a small subset of patients with a very high likelihood of bearing pathogenetic lesions of ATM. As a candidate locus for interaction with ATM, we chose the HRAS1 minisatellite (map position, 11p15). Rare alleles of HRAS1 are strongly associated with a 2-fold increased relative risk of breast cancer[7], and an interaction of the HRAS1 minisatellite with the BRCA1 gene has already been reported that increases the age-related penetrance of ovarian cancer in BRCA1 mutation carriers8. Accordingly, we determined allele states at the HRAS1 minisatellite and a highly informative, intragenic ATM microsatellite locus, NS22, in 66 sib pairs affected with breast cancer. Sib pairs were stratified first by rare/common HRAS1 minisatellite alleles, then by rare-allele-sharing status (identical by state; IBS), then by allele-sharing at NS22, IBS (Table 1). Three sib pairs shared both a rare HRAS1 allele and two ATM alleles IBS. A further 4 sib pairs shared a rare HRAS1 allele and one allele IBS at ATM.

TABLE 1

ATM and CDKN1A Mutations Partitioned by Allele-Sharing in Sib Pairs Affected With Breast Cancer

| HRAS1 Allele-sharing status- Sib Pairs With: | 2 | 1 | 0 | Totals |
|---|---|---|---|---|
| One shared rare allele | 3(2)[a][1][b] | 4(0)[2] | 0(0)[0] | 7(2)[3] 4/7[c] |
| One unshared rare allel | 4(0)[0] | 5(1)[0] | 4(1)[0] | 13(2)[0] 2/13 |
| Only common alleles | 13(1)[1] | 27(4)[3] | 6(0)[1] | 46(5)[5] 10/46 |

[a]ATM Exon 24 mutations detected
[b]CDKN1A mutations detected
[c]total sib pairs in category with any mutation; one sib pair had both ATM exon 24 and CDKN1A mutations Having identified the potentially most appropriate subset for further analysis, we then sequenced DNA of the 3 index cases sharing 2 alleles at ATM with their affected sibs. (The term "index case" refers to the individual of each sib pair who was first identified for purpose of this study.) As candidate mutations, we chose the 5 single-base, exonic polymorphisms[5,6] resulting in nonconservative amino acid changes in the ATM protein. Previous studies had demonstrated that these polymorphisms were apparently not associated with susceptibility to breast cancer, and none exceeded a population prevalence of 3 percent[5,6]. As shown in Table 1, 2 of the 3 cases sharing rare HRAS1 minisatellite and 2 ATM alleles with sibs were also heterozygous for a C-to-G mutation in exon 24 leading to a proline-to-arginine substitution in the ATM protein; see also FIG. 1. The sibs of the two positive index cases, as expected, also demonstrated the exon 24 variant. None of the other sequence ariants was present in any of the 3 index cases or affected sibs, or in the 4 pairs sharing only one ATM allele.

Figure 1A:
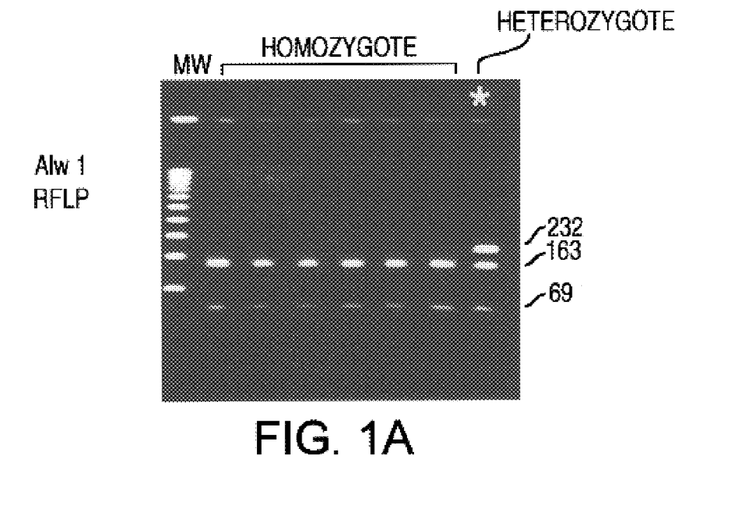
Figure 1B:
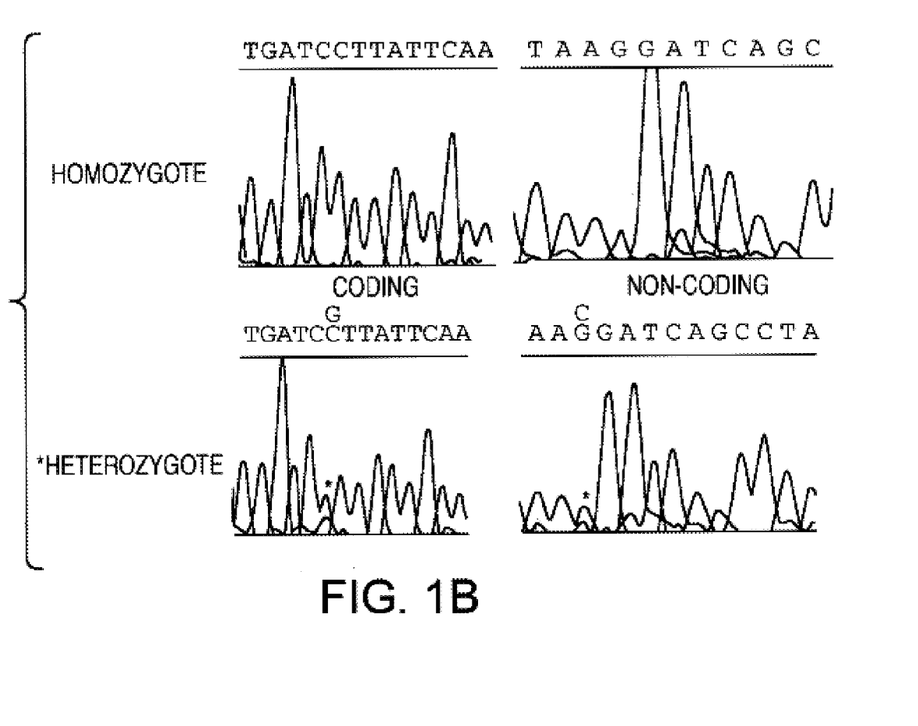

Since this strategy was successful in identifying a polymorphism potentially associated with breast cancer given the presence of an affected sib, we extended exon 24 typing to the entire sample set. The C-to-G mutation resulted in the loss of an Alw I restriction site, so we screened DNA from one member of each sib pair bearing a rare HPAS1 minisatellite allele by PCR amplification, followed by Alw I digestion and gel electrophoresis. For analysis of cases with rare HRAS1 alleles, we chose the sib bearing the rare allele (not necessarily the index case). Two other heterozygotes for the exon 24 mutation were detected from a total of 17 cases examined. Among 46 index cases of sib pairs demonstrating only common HRAS1 alleles, a further 5 heterozygotes appeared. Therefore, 9 of 66 cases identified from sib pairs with breast cancer (9 of 132 independent chromosomes; Table 2) bore a mutation with a previously reported population prevalence of 2.7%[5,6]. All heterozygotes were confirmed by bidirectional dideoxy sequencing of exon 24, as shown in FIG. 1.

TABLE 2

ATM and CDKN1A Mutations in Breast Cancer

| Cases from Affected Sibs | ATM Exon 24 Mutations/Total Alleles | CDKN1A Mutations/Total Alleles |
|---|---|---|
| One shared rare HRAS1 allele[a] | 2/14 | 3/14 |
| One unshared rare HRAS1 allele[a] | 2/26 | 0/26 |
| Only common HRAS1 alleles[b] | 5/92 | 5/92 |
| Total | 9/132 | 8/132 |
| All Ethnic Controls | 4/252 | 11/208 |
| Irish Controls | 3/88 | 3/66 |
| Non-Irish Controls | 1/164 | 8/142 |
| Sporadic Breast Cancer[c] | 2/114 | 1/16 |

[a]Member of sib pair with rare allele was typed for other mutations, or index case if rare allele was shared
[b]Index case was typed
[c]12 leukocyte DNAs, 9 paired tumor/leukocyte DNAs, 36 tumor DNAs These results indicated a breast cancer association for the exon 24 variant that had not previously been observed. To exclude ethnic stratification as the basis of our findings, we typed 126 cancer cases (excluding breast) and cancer-free controls from our DNA bank in which the reported ethnic backgrounds of all four paternal and maternal grandparents were similar to those reported for our cases: English, Scottish, Italian, German, Irish, and Dutch. As shown in Table 2, 4 of 252 alleles among controls demonstrated the exon 24 variant. Of note, 3 of the 4 arose in 88 alleles from Irish controls. Thus, ethnic differences for this variant very likely occur, but these differences were unlikely to be responsible for our result. Given the results from ethnic controls (including Irish), we computed an odds ratio of 4.5 for cases bearing an exon 24 mutation (95% confidence interval, 1.220.5, nominal p=0.02, 2-tail Fisher exact test). For cases that also demonstrated a rare HRAS1 minisatellite allele, the odds ratio was 6.9 (95% CI, 1.2–38.3, p=0.03). The odds ratio for cases with and without rare HRAS1 alleles was 1.9, but did not attain statistical significance (95% CI, 0.49.5, p=0.5).

To investigate the discrepancy between our result and the previous studies with sporadic cases of breast cancer, we also typed 57 cases of sporadic breast cancer from our DNA bank or the tissue bank of the City of Hope. Although all these cases were of Caucasian origin, no further information on ethnic background was available. 36 cases were tumor DNA, 9 matched tumor/leukocyte DNA, and 12 leukocyte DNA. Only 2 of 114 independent alleles showed the C-to-G substitution; in all cases where tumor and leukocyte DNA were paired, the results were concordant (Table 2). Although this frequency was somewhat higher than our controls, it did not differ significantly from the reported prevalence for this mutation. This finding was consistent with our expectation that ascertainment of cases by a positive, first-degree family history of breast cancer would be important in detecting an ATM effect on susceptibility.

Figure 2A:
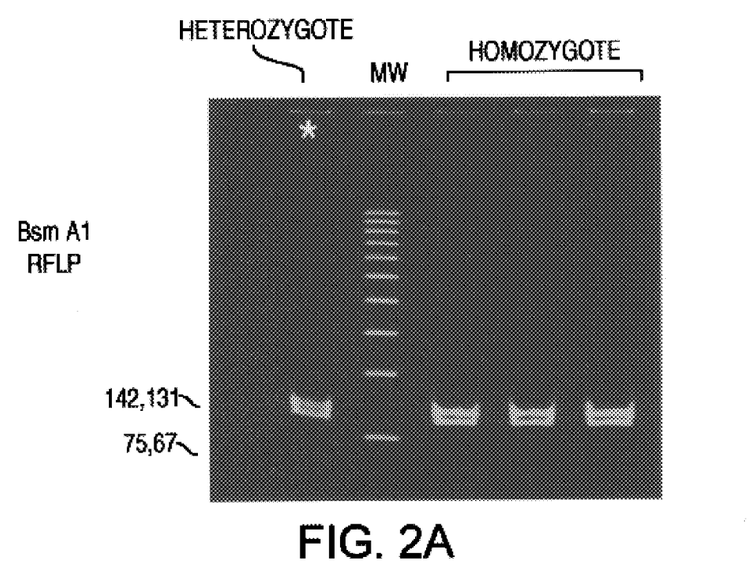
Figure 2B:
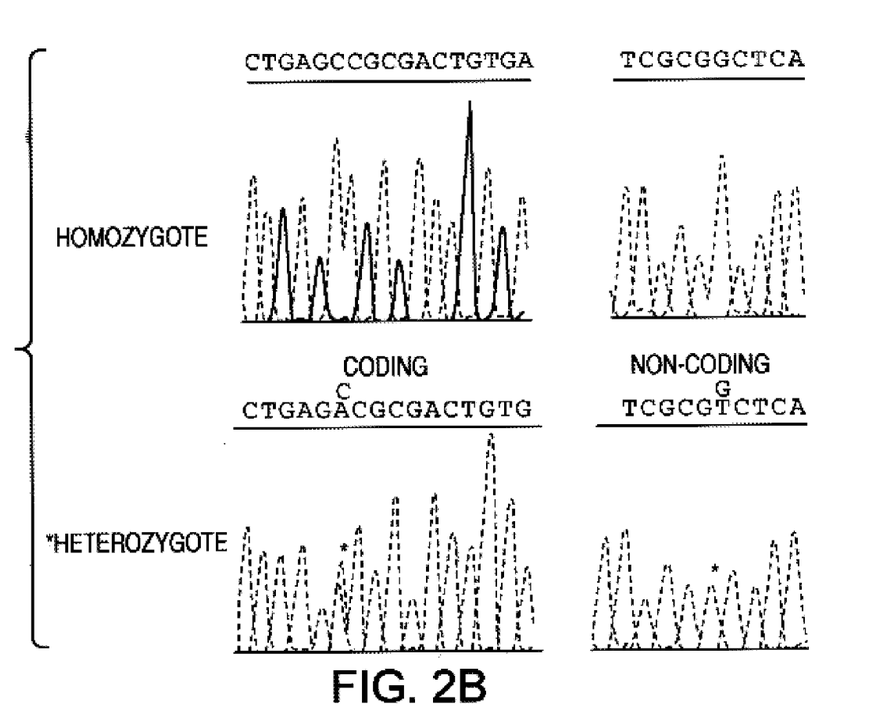

Another gene in the DNA-damage-signaling pathway, downstream of ATM, is CDKN1A (map position, 6p21). It encodes the cyclin-dependent kinase inhibitor, p21$^{CIP1WAF1}$; and several reports have associated an exonic polymorphism of CDKN1A with both breast and lung cancer. Thus, if ATM, CDKN1A, and HRAS1 interact cooperatively together or pairwise to increase the susceptibility to breast cancer, we might expect to demonstrate the allele associated with breast cancer (a C-to-A mutation in codon 31 substituting arginine for serine) within the subset of sibs sharing rare HRAS1 alleles. Accordingly, we typed the 7 index cases and sibs in this category, and in 3 of the 7 pairs, at least one member demonstrated the breast-cancer-associated allele of CDKNLA (FIG. 2; Tables 1 and 2). One sib pair demonstrated a shared rare HRAS1 allele, the shared exon 24 ATM mutation, as well as a shared CDKN1A mutation. Interestingly, one of the 2 cases of sporadic breast cancer that demonstrated the exon 24 mutation also displayed the CDKN1A codon-31 polymorphism. Compared to ethnic controls, however, we did not observe the same association as reported by others. This suggested that any CDKN1A effect might be conditional on ATM status or HRAS1 status, or both.

We have demonstrated that a specific missense variant of the ATM locus is associated with breast cancer. At least two critical factors can account for the different outcomes of the present study and previous analyses[5,6]. The most important of these, as discussed above, is likely to be our ascertainment of cases by history of an affected sib. The second factor is ethnic stratification: It is possible that an ATM effect was previously obscured by a preponderance of controls with an ethnic derivation, such as Irish, bearing a high population prevalence of the exon 24 variant. If this is the case, then one important prediction of our study is that the exon 24 mutation will be a particularly important cause of breast cancer in Irish, and potentially other, subgroups. Indeed, the odds ratio for the ATM variant in our cases and controls increased to 11.9 when an Irish background was eliminated from the analysis (95% CI, 1.6–525.9, p=0.01).

Since the exon 24 mutation has never been detected in any AT family, yet displays a relatively high population prevalence[5,6], it is unlikely that it represents a true AT disease mutation, either in the homozygous state or in combination with one of the known mutations. Recent work of others, however, has suggested one possibility that might account for the biological effect of this variant. Dominant negative "mutations" of the ATM gene that increase radiation sensitivity without affecting cell cycle checkpoints may be created by overexpressing the N-terminal portion of the protein, thereby dissociating different functions of the gene. Therefore, we speculate that the pro>arg substitution may result in a weak dominant negative effect with an abridged phenotypic outcome (presumably moderate radiation sensitivity and susceptibility to breast cancer), but no contribution to other components of the AT phenotype.

METHODS

Characteristics of the study population. Patients diagnosed with breast cancer (Age range 26–84; median, 57) were recruited through the Eastern Cooperative Oncology Group if they had a living sib with breast cancer. Medical and family histories were obtained from patients, and peripheral blood was collected for DNA extraction after informed consent for confidential genetic testing without disclosure of results. 97% of diagnosis reported for index cases were confirmed by submitted pathology reports; 51% of reported sib diagnoses were confirmed by pathology reports. Control DNAs included 126 ethnically matched patients from our local DNA bank (T.G.K.) and both tumor and leukocyte DNAs (57) of breast cancer patients from the City of Hope Pathology Tumor Bank.

HRAS1 Genotyping. DNA was obtained from blood samples using a modified salting-out procedure[18]. 66 sib pairs were genotyped for rare alleles of the HRAS1 minisatellite using a PCR-based assay. Genomic DNA (50 ng) from peripheral blood was amplified in a 50 $\mu$l reaction using 0.4 $\mu$M of the primers MG04 (TET- or FAM-labeled) 5'-GAGCTAGCAGGGCATGCCGC-3' (Seq. ID 9) and MG06 5'-AGCACGGTGTGGAAGGAGCC-3'[18] (Seq. ID 10). TET and FAM are fluorescent dyes in ABI PRISM Dye Terminator Cycle Sequencing Ready Reacation Kit from Perkin Elmer. Reactions also contained 2.5 mM MgCl$_2$, 5% DMSO, 6% glycerol, 1.1 M Betaine, 0.2 $\mu$M each dNTP, 1 $\mu$M DTT in the presence of 2.6 U Expand PCR enzyme (Boehringer Mannheim) in a volume of 50 $\mu$l. Fragments were amplified in a PE9600 thermal cycler under the following conditions: 96° C, 2 min, 10 cycles at 95° C., 30 sec, 58° C., 30 sec, 68° C, 6 min, 17 cycles at 95° C., 30 sec, 58° C., 30 sec, 68° C, 3 min with a 20 sec auto segment extension. TET-labeled products were co-electrophoresed on 5% native Long Ranger gels in the presence of an HRAS1 al-a4, common-allelic, FAM-labeled, reference ladder and GS2500 MW marker (PE/Applied Biosystems) on an ABI377 DNA sequencer. HRAS1 allele designations were determined by comparison of the TET-labeled patient samples to the FAM-labeled reference ladder using Genescan software (v.2.1) (PE/Applied Biosystems).

ATM Genotyping and Mutation Analysis. ATM genotyping used the compound intronic microsatellite locus NS22 (N. Udar and R. Gatti, in preparation). Twenty-five ng genomic DNA was amplified in a 20 $\mu$l reaction with 1 $\mu$M primer, 0.2 $\mu$M dNTP, 1.5 mM MgCl$_s$ in the presence of 1 U Taq 2000 (Stratagene). The primers were 5'-TCTTCTATGAATATAACAGGAGTTGTT-3' (Seq. ID 11) and 5'-GCTTGCAACATCTACTATATATTTTTT-3' (Seq. ID 12). PCR conditions were 94° C., 20 sec, 57° C., 20 sec, 72° C., 30 sec for 30 cycles. Samples were electrophoresed on denaturing 5% Long Ranger sequencing gels on an ABI377 and sized using Genescan and Genotypes software (PE/Applied Biosystems). Previously identified polymorphisms in exon 5 ($C_{146} \rightarrow G$), exon 24 ($C_{3069} \rightarrow G$), exon 31 ($C_{4258} \rightarrow T$), exon 36 ($A_{5071} \rightarrow C$), and exon 49 ($G_{6860} \rightarrow C$) (Genbank accession no. U33841, numbering from base 190, the first base of the start codon) were amplified using PCR primers and conditions previously described[5,6]. PCR products (20 $\mu$l) were purified using Qiaquick columns (Qiagen) and sequenced using AmpliTaq FS polymerase dideoxy terminator chemistry (PE/Applied Biosystems). Heterozygotes were confirmed by sequencing both coding and noncoding strands. Exon 24 heterozygotes were also screened by digesting amplified DNAs (3.5 $\mu$l) with Alw I and electrophoresing products on 6% (w/v) polyacrylamide gels.

CDKN1A Genotyping. Heterozygotes (C$\rightarrow$A, Ser$_{31}\rightarrow$Arg) in CDKN1A were identified by the presence of a newly created Bsm A1 restriction site. The primer pair, CIP/B5' (5'GGATGTCCGTCAGAACCCAT-3') (Seq. ID 13) and CIP1/B3' (5'GGTGCCAGGCCGCCTGCCTC-3') (Seq. ID 14), was used to amplify 25 ng genomic DNA in a 20 $\mu$l reaction with 0.6 $\mu$M primer, 0.2 $\mu$M dNTP, 1 mM MgCl$_2$ in the presence of 0.5 U Taq (Boehringer Mannheim)[12]. A 5 $\mu$l aliquot of the resulting PCR reaction was digested with Bsm A1 and analyzed on 8% polyacrylamide gels. All heterozygotes were confirmed using bidirectional, dideoxy sequencing (dRhodamine, PE/Applied Biosystems) of PCR products.

APPLICATIONS OF THE INVENTION

Where biologically meaningful genetic interactions may be proposed, our method of disease association by locus stratification will have general utility in the analysis of complex genetic disorders. By pursuing candidate interactions rather than simply individual candidate genes, the initial expectation in identifying affected sibs or relatives sharing alleles at candidates loci is that pathogenetic variants will be present at sufficiently high frequencies in these targeted subsets to validate further analysis through larger association/transmission or linkage studies. Candidates for pathogenetic variants may be previously known polymorphisms, as in this study; or the targeted subset may provide alleles for efficient identification of mutations through comprehensive DNA sequencing or other mutation detection techniques. In the case of the ATM exon 24 variant, the effect was unexpectedly of sufficient magnitude to attain statistical significance in a relatively small sample set. The HRAS1 and CDKN1A interactions we have detected, however, will now require confirmation through further testing. Given recent studies implicating BRCAL1[15], BRCA2[16], and ABL[17] in the maintenance of genomic integrity, these and other candidate interactions are already available for additional analysis.

When a pathogenetic allele variant has been identified by our method of disease association by stratification, diagnostic methods can be provided to determine whether an individual is a carrier of the variant. This information can be used to determine whether an individual may be predisposed to cancer, or it can be used in the diagnosis, prognosis or treatment of cancer. The methods will involve taking a tissue, cell or fluid sample from an individual and analyzing the sample to determine whether an individual is a carrier of the variant. Additional useful information may obtained by analyzing the sample to determine whether the individual is a carrier of any allele of any other locus which is known to be or suspected of being associated with cancer or predisposition to cancer. For example, a sample can be analyzed to determine whether the individual is a carrier of the ATM exon 24 variant and either a rare allele of HRAS1 or a mutant allele of CDKN1A having an A for C substitution in codon 31, or both.

A tissue or cell sample can be analyzed for the presence of DNA comprising the ATM exon 24 variant allele or for RNA which is the transcription product of the ATM exon 24 variant, using a labeled oligonucleotide probe which is complementary to and specific for the ATM exon 24 variant or the transcription product. Suitable probes can be synthesized based on the known sequence of the ATM exon 24 (Genbank Accession no. U55722). The DNA or RNA is isolated then digested with one or more suitable restriction enzymes such as EcoRl. The DNA or RNA is transferred by Southern or Northern blotting or dot blotting to a medium suitable for hybridization. The probe is added to the medium and hybrized and the hybridization is detected by label-detecting means. Preferably, the probe is radiolabeled and detected by autoradiography.

Instead of or in addition to digesting the DNA or RNA with restriction enzymes, DNA for the ATM locus or for ATM exon 24 can be amplified by PCR using suitable primers such as those used for exon 24 amplification, as described above[5,6]. The amplified DNA can then be sequenced using dideoxy terminator chemistry as described above to determine the presence of the ATM exon 24 variant. In addition the amplified DNA may be subjected to Alw I RFLP analysis as described above in connection with FIG. 1.

Presence of the ATM exon 24 variant can also be detected by use of high density oligonucleotide arrays on silicon chips, as described by Hacia et al.[19] and references 21–27 cited therein, all of which are incorporated into this disclosure.

Tissue, cell and fluid samples can be analyzed for presence of the expression product of the ATM exon 24 variant by Western blotting or dot blotting, utilizing labeled monoclonal or polyclonal antibody which is specific for the expression product. Tissue samples can also be analyzed by immunohistochemical staining using such antibodies. Such antibodies can be produced by standard techniques which include producing a suitable polypeptide immunogen either synthetically or by recombinant DNA expression in a microorganism, using the immunogen to produce an immune response in a mammal, and harvesting the resulting antibody. A monoclonal antibody specific to the expression product of the ATM exon 24 variant can be produced from cells of the immunized mammal using the technique of Kohler and Milstein.

The methods described for determining presence of the ATM exon 24 variant can be adapted for determining presence of other pathogenetic allele variants.

REFERENCES

1. Swift, M., Reitnauer, P. J., Morrell, D. and Chase, C. L., "Breast and Other Cancers in Families With Ataxia-Telangiectasia," *New Eng. J. Med.* 316, 1289–1294 (1987).
2. Savitsky, K. et al., "A Single Ataxia Telangiectasia Gene With a Product Similar to PI-3 Kinase," *Science* 286, 1749–1753 (1995).
3. Atham, P., Rappaport, R. and Swift, M., "Molecular Genotyping Shows That Ataxia-Telangiectasia Heterozygotes Are Predisposed to Breast Cancer," *Cancer Genet. Cytoaenet.* 92, 130–134 (1996).
4. Fitzgerald, M. G. et al., "Heterozygous ATM Mutations Do Not Contribute to Early Onset of Breast Cancer," *Nature Genet.* 15, 307–310 (1997).
5. Vorechovsky, I. et al., "The ATM Gene and Susceptibility to Breast Cancer: Analysis of 38 Breast Tumors Reveals no Evidence for Mutation," *Cancer Res.* 56, 2726–2732 (1996).
6. Vorechovsky, I. et al., "ATM Mutations in Cancer Families," *Cancer Res.* 56,4130–4133 (1996).
7. Kronitiris, T. G., Devlin B., Karp, D. D., Robert, N. J. and Risch, N., "An Association Between the Risk of Cancer and Mutations in the HRAS1 Minlsatellite Locus," *New Eng. J. Med.* 329, 517–523 (1993).
8. Phelan, C. M. et al., "Ovarian Cancer Risk in BRCA1 Carriers is Modified by the HRAS1 Variable Number of Tandem Repeat (VNTR) Locus," *Nature Genet.* 12, 309–311 (1996).
9. Harper, J. W., Adami, G. R., Wei, N., Keyomarsi, K. and Elledge, S. J., "The p21 Cdk-Interacting Protein Cip1 is a Potent Inhibitor of G1 Cyclin-Dependent Kinases, *Cell* 75, 805–816 (1993).
10. El-Deiry, W. S. et al., "WAF1, a Potential Mediator of p53 Tumor Suppression," *Cell* 75, 817–825 (1993).
11. Chedid, M., Michieli, P., Lengel, C., Huppi, K. and Givol, D., "A Single Nucleotide Substitution at Codon 31 (ser/ag) Defines a Polymorphism in a Highly Conserved Region of the p53-Inducible WAF1/CIP1, *Oncoaene* 9, 3021–3024 (1994).
12. Mousses, S., Ozcelik, H., Lee, P. D., Malkin, D., Bull, S. B. and Andrulis, I. L., "Two Variants of the CIP1/WAF1 Gene Occur Together and Are Associated With Human Cancer," *Hum. Molec. Genet.* 4, 1089–1092 (1995).
13. Sjalander, A., Birgander, R., Rannug, A., Alexandrie, A.-K., Tornling, G. and Beckman, G., "Association Between the p21 Codon 31A1 (arg) Allele and Lung Cancer," *Hum. Hered*. 46, 221–225 (1996).
14. Morgan, S. E., et al., "Fragments of ATM Which Have Dominant-Negative or Complementing Activity," *Mol. Cell. Biol*. 17, 202–2029 (1997).
15. Scully, R. et al., "Association of BRCAL With Rad5l in Mitotic and Meiotic Cells," *Cell* 88, 265–275 (1997).
16. Sharan, S. K. et al., "Embryonic Lethality and Radiation Hypersensitivity Mediated by Rad51 in Mice Lacking Brca2," *Nature* 386, 804–810 (1997).
17. Shafman, T. et al., "Interaction Between ATM Protein and c-Ab1 in Response to DNA Damage," *Nature* 387, 520–532 (1997).
18. Buffone, G. J., "Isolation of DNA From Biological Specimens Without Extraction with Phenol," *Clin. Chem*. 31, 164–165 (1985).
19. Hacia, J. G., et al., "Detection of Heterozygous Mutations in Brca1 Using High Density Oligonucleotide Arrays and Two-Color Fluorescence Analysis," *Nat. Genet*. 14(4), 441–447 (1996).

What is claimed is:

1. A method for rapidly identifying interacting pathogenetic allele variants present in the population that predispose to a disease or that are relevant to diagnosis, prognosis or treatment of a disease which comprises:
   (a) providing a pool of sib pairs affected by a disease;
   (b) selecting from said pool only sib pairs who share both alleles of a first candidate locus,
   (c) further selecting from those sib pairs selected in step (b) sib pairs who share both alleles of a second candidate locus that may participate in an epistatic interaction with the first candidate locus, and
   (d) identifying the interacting pathogenetic allele variants of the candidate loci by genotyping individuals identified in step (c).

2. The method of claim 1, which additionally comprises the step, following step (c), of further selecting from those sib pairs selected in step (c) sib pairs who share both alleles of a third candidate locus that may participate in an epistatic interaction with the first of second candidate locus.

3. The method of claim 1, wherein the sib pairs have cancer.

4. The method of claim 2, wherein the sib pairs have cancer.

5. The method of claim 3, wherein the sib pairs have breast cancer.

6. The method of claim 4, wherein the sib pairs have breast cancer.

7. A method for assessing the likelihood that a subject is predisposed to a disease or diagnosing, prognosing or assessing treatment of a disease in a subject, comprising analyzing a biological sample from the subject to determine the presence or subsence of interacting pathogenetic allelic variants identified according the method of claim 1.

8. A method for determining in an individual the presence of a pathogenetic allelic variant identified by the mehtod of claim 1, which comprises obtaining a biological sample from an individual and detecting the presence of the variant.

9. A method for determining in an individual the presence of interacting pathogenetic allelic variants identified by the method of claim 1, which comprises obtaining a biological sample from an individual and detecting the presence of the variants.

* * * * *

SEQUENCE LISTING

```
<160> NUMBER OF SEQ ID NOS: 14

<210> SEQ ID NO 1
<211> LENGTH: 14
<212> TYPE: DNA
<213> ORGANISM: Homo sapiens

<400> SEQUENCE: 1
tgatccttat tcaa                                                      14

<210> SEQ ID NO 2
<211> LENGTH: 11
<212> TYPE: DNA
<213> ORGANISM: Homo sapiens

<400> SEQUENCE: 2
taaggatcag c                                                         11

<210> SEQ ID NO 3
<211> LENGTH: 14
<212> TYPE: DNA
<213> ORGANISM: Homo sapiens

<400> SEQUENCE: 3
tgatcgttat tcaa                                                      14

<210> SEQ ID NO 4
<211> LENGTH: 13
<212> TYPE: DNA
<213> ORGANISM: Homo sapiens

<400> SEQUENCE: 4
aacgatcagc cta                                                       13

<210> SEQ ID NO 5
<211> LENGTH: 17
<212> TYPE: DNA
<213> ORGANISM: Homo sapiens

<400> SEQUENCE: 5
ctgagccgcg actgtga                                                   17

<210> SEQ ID NO 6
<211> LENGTH: 10
<212> TYPE: DNA
<213> ORGANISM: Homo sapiens

<400> SEQUENCE: 6
tcgcggctca                                                           10

<210> SEQ ID NO 7
<211> LENGTH: 16
```

```
<212> TYPE: DNA
<213> ORGANISM: Homo sapiens

<400> SEQUENCE: 7
ctgagacgcg actgtg                                                    16

<210> SEQ ID NO 8
<211> LENGTH: 10
<212> TYPE: DNA
<213> ORGANISM: Homo sapiens

<400> SEQUENCE: 8
tcgcgtctca                                                           10

<210> SEQ ID NO 9
<211> LENGTH: 20
<212> TYPE: DNA
<213> ORGANISM: Homo sapiens

<400> SEQUENCE: 9
gagctagcag ggcatgccgc                                                20

<210> SEQ ID NO 10
<211> LENGTH: 20
<212> TYPE: DNA
<213> ORGANISM: Homo sapiens

<400> SEQUENCE: 10
agcacggtgt ggaaggagcc                                                20

<210> SEQ ID NO 11
<211> LENGTH: 27
<212> TYPE: DNA
<213> ORGANISM: Homo sapiens

<400> SEQUENCE: 11
tcttctatga atataacagg agttgtt                                        27

<210> SEQ ID NO 12
<211> LENGTH: 27
<212> TYPE: DNA
<213> ORGANISM: Homo sapiens

<400> SEQUENCE: 12
gcttgcaaca tctactatat atttttt                                        27

<210> SEQ ID NO 13
<211> LENGTH: 20
<212> TYPE: DNA
<213> ORGANISM: Homo sapiens

<400> SEQUENCE: 13
ggatgtccgt cagaacccat                                                20

<210> SEQ ID NO 14
<211> LENGTH: 20
<212> TYPE: DNA
<213> ORGANISM: Homo sapiens

<400> SEQUENCE: 14
ggtgccaggc cgcctgcctc                                                20
```